(12) United States Patent
Ichinokawa et al.

(10) Patent No.: US 10,035,793 B2
(45) Date of Patent: Jul. 31, 2018

(54) METHOD FOR PRODUCING 1,2,4-OXADIAZOLE DERIVATIVE

(71) Applicant: ASAHI GLASS COMPANY, LIMITED, Tokyo (JP)

(72) Inventors: Naoki Ichinokawa, Tokyo (JP); Yu Onozaki, Tokyo (JP)

(73) Assignee: ASAHI GLASS COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/556,221

(22) PCT Filed: Mar. 3, 2016

(86) PCT No.: PCT/JP2016/056553
§ 371 (c)(1),
(2) Date: Sep. 6, 2017

(87) PCT Pub. No.: WO2016/143655
PCT Pub. Date: Sep. 15, 2016

(65) Prior Publication Data
US 2018/0037578 A1    Feb. 8, 2018

(30) Foreign Application Priority Data

Mar. 6, 2015   (JP) ................................. 2015-044489
Nov. 16, 2015  (JP) ................................. 2015-223822

(51) Int. Cl.
*C07D 413/04*   (2006.01)
*C07D 333/16*   (2006.01)

(52) U.S. Cl.
CPC ......... *C07D 413/04* (2013.01); *C07D 333/16* (2013.01)

(58) Field of Classification Search
CPC ........................... C07D 413/04; C07D 333/16
See application file for complete search history.

(56) References Cited

U.S. PATENT DOCUMENTS

| 7,576,220 | B2 * | 8/2009 | Horiuchi | C07D 271/06 548/131 |
|---|---|---|---|---|
| 2009/0076101 | A1 | 3/2009 | Ferrigno et al. | |
| 2010/0048648 | A1 | 2/2010 | Bolli et al. | |
| 2010/0240717 | A1 | 9/2010 | Boli et al. | |
| 2014/0039197 | A1 | 2/2014 | Miller et al. | |
| 2014/0235439 | A1 | 8/2014 | Slomczynska et al. | |
| 2015/0225382 | A1 | 8/2015 | Miller et al. | |

FOREIGN PATENT DOCUMENTS

| JP | 2009-523165 A | 6/2009 |
|---|---|---|
| JP | 2009-526830 A | 7/2009 |
| JP | 2010-502693 A | 1/2010 |
| WO | WO 2014/008257 A2 | 1/2014 |
| WO | WO 2014/127195 A1 | 8/2014 |

OTHER PUBLICATIONS

Kandre et al., "Microwave assisted synthesis of 3,5-disubstituted 1,2,4-oxadiazoles from substituted amidoximes and benzoyl cyanides," *Tetrahedron Letters*, 54(27): 3526-3529 (2013).
Patel et al., "Biological Evaluation and Spectral Studies of Asymmetrical 3,5-Disubstituted-1,2,4-Oxadiazoles," *International Research Journal of Pure & Applied Chemistry*, 4(3): 315-326 (2014).
Sondhi et al., "Synthesis anti-inflammatory and anticancer activity evaluation of some pyrazole and oxadiazole derivatives," *Med. Chem. Res.*, 21(10): 3043-3052 (2012).
Japanese Patent Office, International Search Report in International Patent Application No. PCT/JP2016/056553 (dated Jun. 14, 2016), English translation.

* cited by examiner

*Primary Examiner* — Golam M Shameem
(74) *Attorney, Agent, or Firm* — Leydig, Voit & Mayer, Ltd.

(57) ABSTRACT

The invention provides a production method of a 1,2,4-oxadiazole derivative represented by formula (A), which comprises reacting a compound represented by formula (B) and a compound represented by formula (C) in the presence of a basic compound:

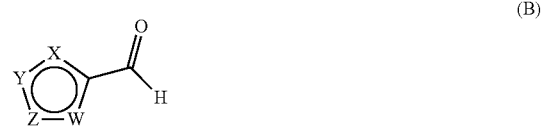

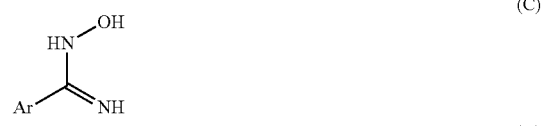

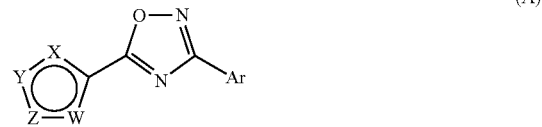

wherein Ar is an aromatic group or an aromatic group having substituent(s); W, X, Y and Z are each independently —S—, —N=, —CH= or —CR=, and one selected from W, X, Y and Z is —S—; and R is an alkyl group having 1 to 5 carbon atoms, an alkoxy group having 1 to 3 carbon atoms, a haloalkyl group having 1 to 3 carbon atoms, a haloalkoxy group having 1 to 3 carbon atoms or a halogen atom.

12 Claims, No Drawings

METHOD FOR PRODUCING 1,2,4-OXADIAZOLE DERIVATIVE

CROSS-REFERENCE TO RELATED APPLICATIONS

This patent application is the U.S. national phase of International Patent Application No. PCT/JP2016/056553, filed on Mar. 3, 2016, which claims the benefit of Japanese Patent Application No. 2015-044489, filed on Mar. 6, 2015, and Japanese Patent Application No. 2015-223822, filed on Nov. 16, 2015, the disclosures of which are incorporated herein by reference in their entireties for all purposes.

TECHNICAL FIELD

The present invention relates to a production method of a 1,2,4-oxadiazole derivative.

BACKGROUND ART 1,2,4-Oxadiazole derivatives having aromatic groups on the 3- and 5-positions are known as physiologically active substances in pharmaceutical and agrochemical fields. As a method of producing the derivatives, a method of reacting an acyl chloride and an aromatic N-hydroxyamidine in the presence of an aqueous base and an organic solvent incompatible with water (see, for example, Patent Document 1).

In addition, it is disclosed that thiophene-2-carboaldehyde and benzamidoxime are reacted in the presence of toluene, a molecular sieve and piperidine to obtain 3-phenyl-5-(thiophen-2-yl)-4,5-dihydro-1,2,4-oxadiazole (see, for example, Patent Document 2).

DOCUMENT LIST

Patent Document

Patent Document 1: WO 2014/008257
Patent Document 2: WO 2014/127195

SUMMARY OF THE INVENTION

Problems to be Solved by the Invention

In the above-mentioned method, the production of the raw material acyl chloride requires many steps, and the raw material acyl chloride is chemically unstable. The aim of the present invention is to provide the production method of 1,2,4-oxadiazole derivatives, which is performed by easy procedures and with high production efficiency.

Means of Solving the Problems

The present inventions to solve the above-mentioned problems are the following inventions:

[1] A method of producing a 1,2,4-oxadiazole derivative represented by the following formula (A), which comprises reacting a compound represented by the following formula (B) and a compound represented by the following formula (C) in the presence of a basic compound;

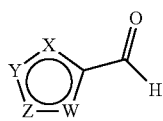
(B)

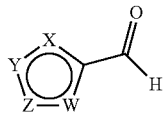
(C)

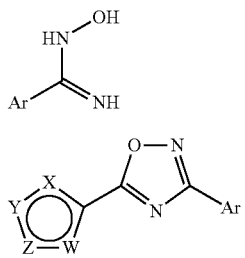
(A)

wherein
Ar is an aromatic group or an aromatic group having substituent(s),
W, X, Y and Z are each independently —S—, —N=, —CH= or —CR=, and one selected from W, X, Y and Z is —S—, and
R is an alkyl group having 1 to 5 carbon atoms, an alkoxy group having 1 to 3 carbon atoms, a haloalkyl group having 1 to 3 carbon atoms, a haloalkoxy group having 1 to 3 carbon atoms or a halogen atom.

[2] A method of producing a 1,2,4-oxadiazole derivative represented by the following formula (A), which comprises reacting a compound represented by the following formula (B) and a compound represented by the following formula (C) in the presence of a basic compound to obtain a reaction product containing a 1,2,4-oxadiazole derivative represented by the following formula (A) and a compound represented by the following formula (G), and then removing the compound represented by the following formula (G) from the reaction product by separation;

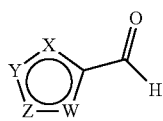
(B)

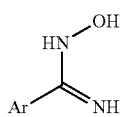
(C)

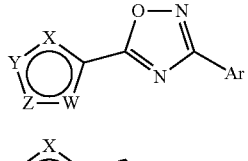
(A)

(G)

wherein
Ar is an aromatic group or an aromatic group having substituent(s),
W, X, Y, and Z are each independently —S—, —N=, —CH= or —CR=, and one selected from W, X, Y and Z is —S—, and
R is an alkyl group having 1 to 5 carbon atoms, an alkoxy group having 1 to 3 carbon atoms, a haloalkyl group having 1 to 3 carbon atoms, a haloalkoxy group having 1 to 3 carbon atoms or a halogen atom.

[3] The method of [2], wherein the compound represented by the formula (G) is subjected to an oxidation reaction to obtain the compound represented by the formula (B), and the obtained compound is reacted with the compound represented by the formula (C).

[4] The method of any one of [1] to [3], wherein the compound represented by the formula (B) is a compound represented by the following formula (B¹), and the 1,2,4-oxadiazole derivative represented by the formula (A) is a compound represented by the following formula (A¹);

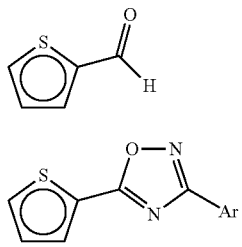

wherein Ar is as defined in [1].

[5] The method of any one of [1] to [4], wherein Ar is a phenyl group or a phenyl group having substituent(s).

[6] The method of any one of [1] to [5], wherein the reaction of the compound represented by the formula (B) and the compound represented by the formula (C) is performed in the presence of a solvent.

[7] The method of any one of [1] to [6], wherein the reaction of the compound represented by the formula (B) and the compound represented by the formula (C) is performed with dehydration.

[8] The method of any one of [1] to [7], wherein the compound represented by the formula (B) is reacted in an amount exceeding 1 mol, per 1 mol of the compound represented by the formula (C).

[9] The method of any one of [1] to [8], wherein the basic compound is at least one inorganic basic compound selected from the group consisting of an alkali metal carbonate, an alkaline-earth metal carbonate, an alkali metal hydroxide and an alkaline-earth metal hydroxide.

[10] The method of [9], wherein the inorganic basic compound is used in an amount of 2 mol or less, per 1 mol of the compound represented by the formula (C).

[11] The method of any one of [1] to [8], wherein the basic compound is an organic basic compound, and the organic basic compound is used in an amount of 0.3 mol or more, per 1 mol of the compound represented by the formula (C).

[12] The method of any one of [1] to [11], wherein the compound represented by the formula (C) is obtained by reacting a compound represented by the following formula (F) with hydroxylamine, and then the obtained compound is reacted with the compound represented by the formula (B);

wherein Ar is as defined in [1].

[13] The method of any one of [1] to [12], wherein the compound represented by the formula (C) is subjected to dehydration, and then reacted with the compound represented by the formula (B).

[14] The method of [12] or [13], wherein the compound represented by the formula (F) is reacted with hydroxylamine in a solvent to obtain a mixture of the compound represented by the formula (C) and the solvent, and then the obtained mixture is reacted with the compound represented by the formula (B).

[15] A method of producing a compound represented by the following formula (G), which comprises reacting a compound represented by the following formula (B) and a compound represented by the following formula (C) in the presence of a basic compound;

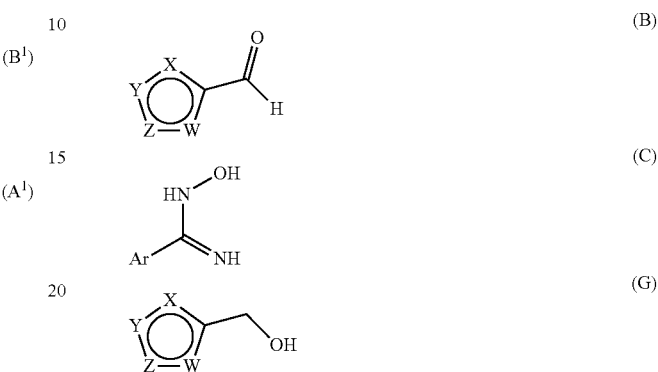

wherein

Ar is an aromatic group or an aromatic group having substituent(s),

W, X, Y and Z are each independently —S—, —N═, —CH═ or —CR═, and one selected from W, X, Y and Z is —S—, and R is an alkyl group having 1 to 5 carbon atoms, an alkoxy group having 1 to 3 carbon atoms, a haloalkyl group having 1 to 3 carbon atoms, a haloalkoxy group having 1 to 3 carbon atoms or a halogen atom.

Effect of the Invention

According to the present invention, the production method of 1,2,4-oxadiazole derivatives, which is performed by easy procedures and with high production efficiency, can be provided.

DESCRIPTION OF EMBODIMENTS

In the present specification, a 1,2,4-oxadiazole derivative represented by the following formula (A) may also be referred to as oxadiazole derivative A. A compound represented by the following formula (B) may also be referred to as compound B. Other compounds represented by other formulas may also be referred to likewise. Numerical range shown by using "to" means the range including the numerical values described before and after "to" as minimum and maximum values.

In the present specification, the "halogen atom" means a fluorine atom, a chlorine atom, a bromine atom or an iodine atom.

In the present specification, the "alkyl group having 1 to 5 carbon atoms" means a linear or branched saturated hydrocarbon group having 1 to 5 carbon atoms, and examples thereof include methyl, ethyl, propyl, isopropyl, butyl, isobutyl, sec-butyl, tert-butyl, pentyl, isopentyl, neopentyl, 1-ethylpropyl and the like.

In the present specification, the "alkyl group having 1 to 3 carbon atoms" means a linear or branched saturated hydrocarbon group having 1 to 3 carbon atoms, and examples thereof include methyl, ethyl, propyl and isopropyl.

In the present specification, the "alkenyl group having 2 to 5 carbon atoms" means a linear or branched unsaturated hydrocarbon group having at least one double bond and having 2 to 5 carbon atoms, and examples thereof include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl and the like.

In the present specification, the "alkynyl group having 2 to 5 carbon atoms" means a linear or branched unsaturated hydrocarbon group having at least one triple bond and having 2 to 5 carbon atoms, and examples thereof include ethynyl, 1-propynyl, 2-propynyl, 1-butynyl, 2-butynyl, 3-butynyl, 1-pentynyl, 2-pentynyl, 3-pentynyl, 4-pentynyl and the like.

In the present specification, the "alkoxy group having 1 to 5 carbon atoms" means an oxy group substituted by the "alkyl group having 1 to 5 carbon atoms", and examples thereof include methoxy, ethoxy, propoxy, isopropoxy, butoxy, isobutoxy, sec-butoxy, tert-butoxy, pentyloxy, isopentyloxy, neo-pentyloxy, 1-ethylpropyloxy and the like.

In the present specification, the "alkoxy group having 1 to 3 carbon atoms" means an oxy group substituted by the "alkyl group having 1 to 3 carbon atoms", and examples thereof include methoxy, ethoxy, propoxy and isopropoxy.

In the present specification, the "haloalkyl group having 1 to 5 carbon atoms" means the "alkyl group having 1 to 5 carbon atoms" substituted by one or more (preferably 1 to 5, more preferably 1 to 3) "halogen atoms", and examples thereof include fluoromethyl, difluoromethyl, trifluoromethyl, 1-fluoroethyl, 2-fluoroethyl, 2,2-difluoroethyl, 2,2,2-trifluoroethyl, 1-fluoropropyl, 2-fluoropropyl, 3-fluoropropyl, chloromethyl, 2-chloroethyl, 3-chloropropyl, bromomethyl, 4-fluorobutyl, 5-fluoropentyl and the like.

In the present specification, the "haloalkyl group having 1 to 3 carbon atoms" means the "alkyl group having 1 to 3 carbon atoms" substituted by one or more (preferably 1 to 5, more preferably 1 to 3) "halogen atoms", and examples thereof include fluoromethyl, difluoromethyl, trifluoromethyl, 1-fluoroethyl, 2-fluoroethyl, 2,2-difluoroethyl, 2,2,2-trifluoroethyl, 1-fluoropropyl, 2-fluoropropyl, 3-fluoropropyl, chloromethyl, 2-chloroethyl, 3-chloropropyl, bromomethyl and the like.

In the present specification, the "haloalkoxy group having 1 to 5 carbon atoms" means the "alkoxy group having 1 to 5 carbon atoms" substituted by one or more (preferably 1 to 5, more preferably 1 to 3) "halogen atoms", and examples thereof include fluoromethoxy, difluoromethoxy, trifluoromethoxy, 1-fluoroethoxy, 2-fluoroethoxy, 2,2-difluoroethoxy, 2,2,2-trifluoroethoxy, 1-fluoropropoxy, 2-fluoropropoxy, 3-fluoropropoxy, chloromethoxy, 2-chloroethoxy, 3-chloropropoxy, bromomethoxy, 4-fluorobutoxy, 5-fluoropentyloxy and the like.

In the present specification, the "haloalkoxy group having 1 to 3 carbon atoms" means the "alkoxy group having 1 to 3 carbon atoms" substituted by one or more (preferably 1 to 5, more preferably 1 to 3) "halogen atoms", and examples thereof include fluoromethoxy, difluoromethoxy, trifluoromethoxy, 1-fluoroethoxy, 2-fluoroethoxy, 2,2-difluoroethoxy, 2,2,2-trifluoroethoxy, 1-fluoropropoxy, 2-fluoropropoxy, 3-fluoropropoxy, chloromethoxy, 2-chloroethoxy, 3-chloropropoxy, bromomethoxy and the like.

In the present specification, the "alkylsulfonyl group having 1 to 5 carbon atoms" means a sulfonyl group to which the "alkyl group having 1 to 5 carbon atoms" is bonded, and examples thereof include methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl, isopentylsulfonyl, neo-pentylsulfonyl, 1-ethylpropylsulfonyl and the like.

In the present specification, the "aryl group having 6 to 14 carbon atoms" means an aromatic hydrocarbon group having 6 to 14 carbon atoms, and examples thereof include phenyl, 1-naphthyl, 2-naphthyl, 1-anthryl, 2-anthryl, 9-anthryl, 1-phenanthryl, 2-phenanthryl, 9-phenanthryl and the like. Among them, preferred is an "aryl group having 6 to 10 carbon atoms".

In the present specification, the "aryl group having 6 to 10 carbon atoms" means an aromatic hydrocarbon group having 6 to 10 carbon atoms, and examples thereof include phenyl, 1-naphthyl, 2-naphthyl and the like.

In the present specification, the "acyl group having 2 to 6 carbon atoms" means a carbonyl group to which the "alkyl group having 1 to 5 carbon atoms" or "alkoxy group having 1 to 5 carbon atoms" is bonded, and examples thereof include alkyl-carbonyl groups wherein the alkyl has 1 to 5 carbon atoms, such as acetyl, propanoyl, butanoyl, 2-methylpropanoyl, pentanoyl, 3-methylbutanoyl, 2-methylbutanoyl, 2,2-dimethylpropanoyl, hexanoyl and the like; and alkoxy-carbonyl groups wherein the alkoxy has 1 to 5 carbon atoms, such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and the like.

In the present specification, the "aromatic group" means an aryl group having 6 to 14 carbon atoms or a heteroaryl group.

In the present specification, the "heteroaryl group" means a 5- to 12-membered (preferably 5- to 10-membered) aromatic heterocyclic group containing at least one (preferably 1 to 4) hetero atom selected from the group consisting of an oxygen atom, a nitrogen atom and a sulfur atom, as a ring-constituting atom, in addition to carbon atom(s). Preferable examples of the "heteroaryl group" include 5- to 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like;
8- to 12-membered fused polycyclic (preferably bi- or tri-cyclic) aromatic heterocyclic groups such as benzothienyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl and the like.

In the present invention, for the production of oxadiazole derivative A, compound B and compound C are selected as raw materials, and are reacted.

(B)

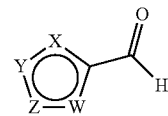

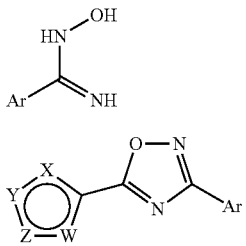

wherein

Ar is an aromatic group or an aromatic group having substituent(s),

W, X, Y and Z are each independently —S—, —N═, —CH═ or —CR═, and one selected from W, X, Y and Z is —S—, and R is an alkyl group having 1 to 5 carbon atoms, an alkoxy group having 1 to 3 carbon atoms, a haloalkyl group having 1 to 3 carbon atoms, a haloalkoxy group having 1 to 3 carbon atoms or a halogen atom.

Compound B is superior in handling property due to its chemical stability, and can be easily produced or available. That is to say, the production method of the present invention is a method using a chemically stable and easily available compound as a raw material, and a method of producing the objective compound in a shorter step than conventional method. In the present invention, compound B and compound C are reacted in the presence of a basic compound, and thereby, dihydrooxadiazole ring-forming reaction by dehydration condensation of compound B and compound C, and the sequence oxidation reaction of the dihydrooxadiazole ring efficiently proceed, and the desired oxadiazole derivative A can be obtained with excellent conversion rate and selectivity.

[Compound B]

In the formula (B), W, X, Y and Z are each independently —S—, —N═, —CH═ or —CR═, and one selected from W, X, Y and Z is —S—. That is to say, the 5-membered ring moiety in compound B is a 5-membered aromatic heterocycle essentially containing at least one carbon atom and one sulfur atom, and optionally containing a nitrogen atom, as a ring-constituting atom. Compound B has structure in which a formyl group is bonded to the one of the ring-constituting carbon atom(s) in the 5-membered aromatic heterocycle. In addition, a hydrogen atom or a substituent (R), preferably a hydrogen atom, is bond to the other ring-constituting carbon atom in the 5-membered aromatic heterocycle. In compound B, X or W is preferably —S—.

Specific examples of the 5-membered aromatic heterocycle include the following heterocycles.

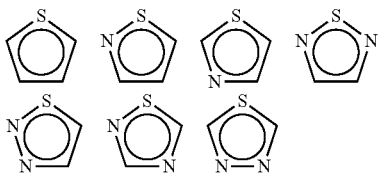

Examples of the 5-membered aromatic heterocyclic group include a group in which one hydrogen atom bonded to the ring-constituting carbon atom is removed from the above-mentioned 5-membered aromatic heterocycle. The position of the bond is not particularly limited as long as it is on the ring-constituting carbon atom. The 5-membered aromatic heterocyclic group is preferably a thienyl group. The thienyl group may be a thiophen-2-yl group or a thiophen-3-yl group, preferably a thiophen-2-yl group from the aspect of utility such as physiological activity of oxadiazole derivative A.

In the formula (B), R is an alkyl group having 1 to 5 carbon atoms, an alkoxy group having 1 to 3 carbon atoms, a haloalkyl group having 1 to 3 carbon atoms, a haloalkoxy group having 1 to 3 carbon atoms or a halogen atom. R is preferably an alkyl group having 1 to 3 carbon atoms, a haloalkoxy group having 1 to 3 carbon atoms or a halogen atom, more preferably a methyl group, a trifluoromethoxy group or a halogen atom. When the number of R is two or more, each R may be the same or different.

Preferable examples of the compound B include thiophene-2-carboaldehyde, thiophene-3-carboaldehyde, thiazole-2-carboaldehyde, thiazole-4-carboaldehyde, thiazole-5-carboaldehyde, 2,1,3-thiadiazole-4-carboaldehyde, 1,2,3-thiadiazole-4-carboaldehyde, 1,2,3-thiadiazole-5-carboaldehyde, 1,2,4-thiadiazole-3-carboaldehyde, 1,2,4-thiadiazole-5-carboaldehyde, 1,3,4-thiadiazole-2-carboaldehyde and the like, and particularly preferred is thiophene-2-carboaldehyde.

Compound B can be easily produced from a known compound by a known method, or is industrially easily available.

[Compound C]

Compound C is in equilibrium with a compound represented by the formula (C') as shown below. In the present specification, they are hereinafter collectively referred to as compound C. The wavy lines in formula (C') mean that the configuration of OH relating to the double bond may be E or Z.

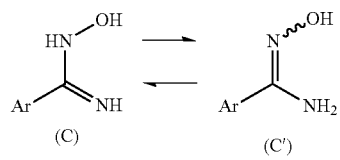

In the present specification, the "reaction of compound B and compound C", the "reaction of compound B and compound C'" and the "reaction of compound B and a mixture of compound C and compound C'" are hereinafter collectively referred to as the "reaction of compound B and compound C".

In formula (C), Ar is an aromatic group or an aromatic group having substituent(s).

The substituent of the "aromatic group having substituent(s)" is not particularly limited as long as it is monovalent group which does not adversely influence the reaction of the present invention. Examples of the substituent include an alkyl group having 1 to 5 carbon atoms, an alkenyl group having 2 to 5 carbon atoms, an alkynyl group having 2 to 5 carbon atoms, an alkoxy group having 1 to 5 carbon atoms, an aryl group having 6 to 10 carbon atoms, a haloalkyl group having 1 to 5 carbon atoms, a haloalkoxy group having 1 to 5 carbon atoms, an acyl group having 2 to 6 carbon atoms, a halogen atom, a hydroxy group, a sulfanyl group, an amino group, an alkylsulfonyl group having 1 to 5 carbon atoms and the like. Preferred are an alkyl group having 1 to 3 carbon atoms, an alkoxy group having 1 to 3 carbon atoms, a haloalkyl group having 1 to 3 carbon atoms, a haloalkoxy group having 1 to 3 carbon atoms, a halogen atom and a cyano group, and more preferred are a methyl group, a fluoromethyl group, a trifluoromethyl group, a methoxy group, a trifluoromethoxy group, a halogen atom, a cyano group and a formyl group, and particularly preferred are a methyl group and a halogen atom.

When the number of the substituent in Ar is two or more, each substituent may be the same or different. The number of the substituent is preferably 1 to 5, more preferably 1 to 3. In addition, the substitution position is not particularly limited.

When Ar has two substituents, the two substituent are optionally bonded to each other to form a fused ring together with Ar. The ring formed by the two substituent bonded to each other may be an aromatic ring or a non-aromatic ring, and it may be a carbocycle or a heterocycle containing at least one hetero atom selected from the group consisting of an oxygen atom, a nitrogen atom and a sulfur atom. Specific examples of the Ar include benzofuryl and the like.

Ar is preferably an aryl group having 6 to 14 carbon atoms or an aryl group having 6 to 14 carbon atoms and having substituent(s), more preferably an aryl group having 6 to 10 carbon atoms or an aryl group having 6 to 10 carbon atoms and having substituent(s), further more preferably a phenyl group or a phenyl group having substituent(s), still more preferably a phenyl group, or a phenyl group having substituent(s) selected from an alkyl group having 1 to 3 carbon atoms, an alkoxy group having 1 to 3 carbon atoms, a haloalkyl group having 1 to 3 carbon atoms, a haloalkoxy group having 1 to 3 carbon atoms, a halogen atom and a cyano group, even more preferably a phenyl group, or a phenyl group having substituent(s) selected from a methyl group, a fluoromethyl group, a trifluoromethyl group, a methoxy group, a trifluoromethoxy group, a halogen atom, a cyano group and a formyl group. Preferable specific examples of the phenyl group having substituent(s) include an o-, m- or p-fluorophenyl group, an o-, m- or p-chlorophenyl group, an o-, m- or p-tolyl group, an o-, m- or p-fluoromethylphenyl group and a difluorophenyl group, a trifluorophenyl group. Ar is most preferably a phenyl group from the aspect of utility such as physiological activity of oxadiazole derivative A.

Compound C used for the reaction with compound B is preferably subjected to dehydration treatment. The dehydration treatment can be performed according to a known method, for example, azeotropic dehydration treatment, dehydration treatment using a dehydrating agent molecular sieve and the like, and the like. The water content rate of the compound C used for the reaction with compound B is preferably 5 mass % or less, more preferably 1 mass % or less.

Compound C is industrially easily available. Alternatively, compound C can be produced by reacting a compound represented by the following formula (F) with hydroxylamine. Ar in the formula is as defined above.

Ar—CN  (F)

The reaction is preferably performed in the presence of a solvent, and can be performed according to the method described in literature (e.g., Organic Letters, 16(3), 892-895; 2014). The hydroxylamine may be used in the form of an aqueous solution. Examples of the solvent include alcohols such as ethanol, t-butanol, t-amyl alcohol and the like, ethers such as tetrahydrofuran, 2-methyltetrahydrofuran and the like, water and the like. The amount of the solvent is preferably 1 to 5-fold amount, particularly preferably 1 to 3-fold amount relative to the volume of compound F. The lower limit of the reaction temperature is preferably 20° C., more preferably 30° C. The upper limit of the reaction temperature is preferably 100° C., more preferably 80° C. When the reaction temperature is the lower limit or above, the reaction can proceed rapidly, and when the reaction temperature is the upper limit or below, the production of by-product can be reduced. While the reaction time varies depending on the reaction temperature or the reaction pressure, it is preferably 1 to 10 hr. The reaction pressure may be normal pressure, increased pressure or reduced pressure, preferably normal pressure or increased pressure. The reaction pressure is preferably 0.01 to 0.5 MPa (gauge pressure). The reaction atmosphere may be an air atmosphere or an inert gas atmosphere such as nitrogen and the like.

The reaction of compound B and compound C in the present invention is preferably performed under a condition in which the water content in the reaction system is as small as possible, for the below-mentioned reason. Therefore, it is preferable that, the water is removed after the reaction of compound F and hydroxylamine to obtain compound C having as small water content as possible.

The removal of the water is performed by isolating compound C after the reaction, or by dehydration treatment after the reaction.

For example, when the reaction of compound F and hydroxylamine is performed in water as a solvent, it is preferable that the water is removed from the mixture of the water and compound C to obtain compound C, and the obtained compound C is reacted with compound B. The water content rate of compound C after the removal of the water is preferably 5 mass % or less, more preferably 1 mass % or less. The removal of the water can be performed by separation operation, preferably followed by dehydration treatment.

When the reaction of compound F and hydroxylamine is performed in the presence of a solvent, the mixture containing compound C and the solvent is obtained. The mixture is the solvent solution containing compound C, when compound C is dissolved in the solvent. The water content of the mixture after the removal of the water is preferably 5 mass % or less, more preferably 1 mass % or less, relative to the total mass of the mixture. The removal of the water can be performed by a method of isolating compound C from the mixture, or by a method of subjecting the mixture to dehydration treatment, preferably the latter method. In the case of the latter method, compound C in the form of a mixture can be reacted with compound B, without isolation of compound C from the mixture containing compound C and the solvent. Therefore, the latter method can be an efficient production method. That is to say, it is preferable that compound F and hydroxylamine are reacted in a solvent to obtain a mixture of compound C and the solvent, and the obtained compound C in the form of a mixture with the solvent is reacted with compound B, more preferably the mixture of compound C and the solvent is subjected to dehydration treatment, and compound C in the form of a mixture with the solvent is reacted with compound B. According the production method, the reaction of the next step can be performed in the form of a mixture, using the same reactor, and thereby the efficiency in production step can be significantly improved.

The dehydration treatment can be performed by azeotropic dehydration treatment, or dehydration treatment using a dehydrating agent such as molecular sieve and the like. When dehydration treatment is performed by azeotropic dehydration treatment, the solvent used for the reaction of compound F and hydroxylamine is preferably a solvent capable of azeotropically dehydrating the mixture, that is, a solvent capable of forming an azeotropic mixture with water. Examples of the solvent include ethanol, t-butanol, t-amyl alcohol and the like.

[Oxadiazole Derivative A]

Oxadiazole derivative A, which is the objective compound of the production method of the present invention, is a compound represented by the formula (A). The definitions and preferable embodiments of Ar, W, X, Y and Z in the formula are as described above.

Oxadiazole derivative A is preferably a compound represented by the following formula (A¹). Ar in the formula is as defined above.

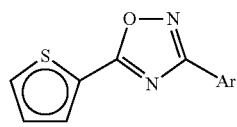
(A¹)

Specific examples of the oxadiazole derivative A include the following compounds.

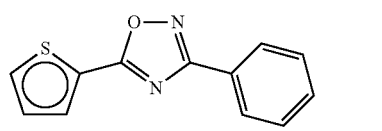
(1)

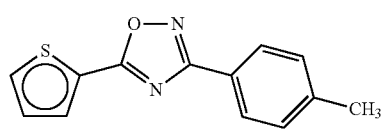
(2)

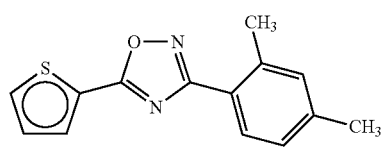
(3)

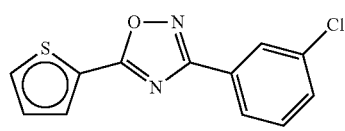
(4)

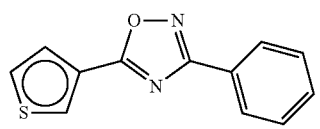
(5)

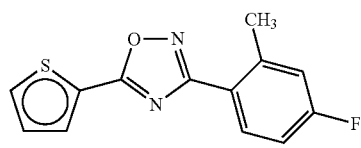
(6)

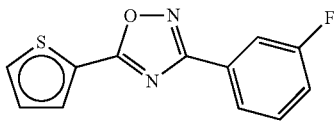
(7)

[Production Method of the Present Invention]

The production method of oxadiazole derivative A in the present invention is performed by reacting compound B and compound C in the presence of a basic compound.

The basic compound may be an organic basic compound or an inorganic basic compound.

Examples of the inorganic basic compound include alkali metal or alkaline-earth metal salts such as alkali metal or alkaline-earth metal carbonates, alkali metal or alkaline-earth metal hydrogencarbonates and the like; alkali metal or alkaline-earth metal hydroxides, and the like. Specific examples thereof include alkali metal or alkaline-earth metal carbonates such as potassium carbonate, sodium carbonate, calcium carbonate and the like; alkali metal or alkaline-earth metal hydrogencarbonates such as potassium hydrogencarbonate, sodium hydrogencarbonate, calcium hydrogencarbonate and the like; alkali metal or alkaline-earth metal hydroxides such as potassium hydroxide, sodium hydroxide, calcium hydroxide and the like, and the like.

Examples of the organic basic compound include lower amines such as triethylamine, piperidine, pyrrolidine, morpholine and the like; basic aromatic heterocyclic compounds such as pyridine and the like; alkali metal or alkaline-earth metal alkoxides such as sodium methoxide, sodium ethoxide, potassium methoxide, potassium ethoxide, potassium t-butoxide and the like; alkali metal amides such as lithium diisopropylamide, potassium hexamethyldisilazide and the like, and the like.

The basic compound is preferably an inorganic basic compound, more preferably an alkali metal or alkaline-earth metal carbonate, or an alkali metal or alkaline-earth metal hydroxide, further more preferably an alkali metal carbonate or hydroxide, still more preferably potassium carbonate or potassium hydroxide, particularly preferably potassium hydroxide, from the aspect of reactivity. The basic compound may be used alone or in combination of two or more kinds thereof.

When the inorganic basic compound is used, compound C can be efficiently activated because the reaction system become highly basic. Therefore, oxadiazole derivative A can be efficiently produced. According the present inventors' studies, use of potassium hydroxide or potassium carbonate shows particularly remarkable effect.

When the inorganic basic compound is used, the amount of basic compound to be used is preferably 0.01 to 2 mol, per 1 mol of compound B, and it is preferably 2 mol or less, more preferably 1 mol or less, further more preferably 0.5 mol or less, particularly preferably 0.3 mol or less, per 1 mol of compound C, and is preferably 0.01 mol or more, more preferably 0.05 mol or more, particularly preferably 0.08 mol or more, per 1 mol of compound C. When the moles of compound B and compound C are different, the amount of the basic compound is determined on the basis of compound C. By setting the amount of the inorganic basic compound at the above-mentioned range, the side reaction can be reduced, and the yield can be improved.

An organic base compound may be used as a basic compound. The organic basic compound is preferably a primary amine or a secondary amine. The primary amine or secondary amine is reacted with compound B to give the corresponding activated imine, and the imine can be reacted with compound C. Examples of the primary amine or secondary amine include dimethylamine, diethylamine, piperidine, pyrrolidine, morpholine and the like, and preferred are cyclic amines such as piperidine, pyrrolidine, morpholine and the like. By use of a cyclic amine having small steric hindrance, the reaction efficiently proceeds.

When the organic basic compound is used, the amount is preferably 0.2 to 4 mol, per 1 mol of compound B, and it is preferably 4 mol or less, more preferably 3 mol or less, further more preferably 2 mol or less, particularly preferably 1.5 mol or less, per 1 mol of compound C, and is preferably 0.3 mol or more, more preferably 0.5 mol or more, particularly preferably 0.7 mol or more, per 1 mol of compound C. When the moles of compound B and compound C are different, the amount of the basic compound is determined on the basis of compound C. By setting the amount of the organic basic compound at the above-mentioned range, the side reaction can be reduced, and the yield can be improved.

The basic compound in the present invention is preferably an inorganic base compound from the aspect that the reaction efficiently proceeds even if the amount of the basic compound is small, and that post-treatment after the reaction is easy.

The basic compound can be directly used, or can be dissolved in a solvent. Examples of the solvent include one or two more solvents selected form the below-mentioned reaction solvent.

The reaction of compound B and compound C can be performed by contacting these compound to each other. The contact is performed by a method of dissolving the one compound in a solvent, and adding the solution to the other compound; a method of adding compound B and compound C to a solvent, and stirring the mixture; and the like. In addition, the reaction may be in batch system or in continuous system.

The optimal condition depending on the kinds of compound B and compound C is preferably applied to the reaction of compound B and compound C.

The reaction conditions such as the reaction temperature, reaction time, reaction pressure, reaction atmosphere and the like for the reaction of compound B and compound C can be appropriately changed depending on the kinds of compound B, compound C, the basic compound and the solvent, and the like. Generally, the lower limit of the reaction temperature is preferably 40° C., more preferably 50° C., further more preferably 90° C., particularly preferably 100° C., and the upper limit of the reaction temperature is preferably 160° C., more preferably 140° C., particularly preferably 120° C.

When the lower limit of the reaction temperature is the above-mentioned temperature, the reaction easily proceeds rapidly. When the upper limit of the reaction temperature is the above-mentioned temperature, by-products are hardly generated.

While the reaction time varies depending on the reaction temperature and the reaction pressure, it is preferably 1 to 30 hr. The reaction pressure may be normal pressure, increased pressure or reduced pressure. The reaction atmosphere may be an air atmosphere, or an inert gas atmosphere such as nitrogen is and the like.

The reaction of compound B and compound C is preferably performed in the presence of a solvent. Preferable examples of the solvent include alcohols such as ethanol, propanol, isopropanol, butanol, t-butanol, amyl alcohol, t-amyl alcohol, hexanol, octanol and the like; aromatic hydrocarbons such as toluene, anhydrous toluene and the like; aprotic polar solvents such as dimethyl sulfoxide, dimethylformamide, sulfolane, dioxane and the like, and the like. The solvent is more preferably at least one selected from the group consisting of an alcohol, an aromatic hydrocarbon and an aprotic polar solvent, particularly preferably an alcohol.

The number of the carbon atom of the alcohol is preferably 1 to 8, more preferably 2 to 8, further more preferably 4 to 6. In addition, the alcohol is preferably a tertiary alcohol, particularly preferably t-amyl alcohol, from the aspect of reaction efficiency.

When compound F and hydroxylamine are reacted in a solvent to obtain compound C, and compound C in the form of a mixture is reacted with compound B, without isolation, the same solvent as that for the production of compound C is preferably used for the reaction of compound B and compound C.

Since the water generated in the reaction of compound B and compound C is preferably removed for the below-mentioned reason, the solvent is preferably a solvent capable of forming an azeotropic mixture with water, more preferably an alcohol capable of forming an azeotropic mixture with water. Specifically, the solvent is preferably at least one selected from the group consisting of ethanol, t-butanol and t-amyl alcohol.

Since the solvent used for the reaction of compound B and compound C may remain in the below-mentioned oxidation step of compound G, the solvent is more preferably a tertiary alcohol from the aspect of reduction of the side reaction in the oxidation step.

The amount of the solvent is preferably 0.2 to 15-fold amount, relative to the volume of compound B, and is preferably 0.2 to 15-fold amount, particularly preferably 1 to 10-fold amount, relative to the volume of compound C. When the volume of compound B and compound C are different, the amount of the solvent is preferably determined on the basis of compound C.

The water is generated in the reaction of compound B and compound C. By removing the generated water, the equilibrium of the reaction can move to the production side. In addition, by removing the generated water, the below-mentioned hydrolysis reaction of the intermediate product compound D, and the like can be reduced. Therefore, in the present invention, the reaction of compound B and compound C is preferably performed with dehydration. As a dehydration method, publicly or commonly known methods such as a method in the presence of a dehydrating agent, a method of evaporating water by azeotropic treatment and the like can be employed. Examples of the dehydrating agent include molecular sieve and the like. In addition, when the basic compound made present in the reaction of compound B and compound C is a compound having a dehydrating action, the dehydration can be performed without a dehydrating agent.

Oxadiazole derivative A is obtained by the reaction of compound B and compound C, and the following compound G is contained in the reaction product as a by-product. W, X, Y and Z in the formula are as defined above.

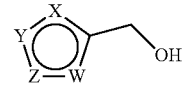

(G)

Compound G is a compound produced by reduction of compound B. In the present invention, compound G is preferably removed by separation from the reaction product containing oxadiazole derivative A and compound G to obtain the purified oxadiazole derivative A.

The production mechanism of compound G is considered as follows. Theoretically, 1 mol of compound B and 1 mol of compound C are reacted to give compound D, and then, compound D is oxidized by compound B in the presence of a basic compound to give oxadiazole derivative A. At this time, compound B which oxidizes compound D is converted to compound G by reduction.

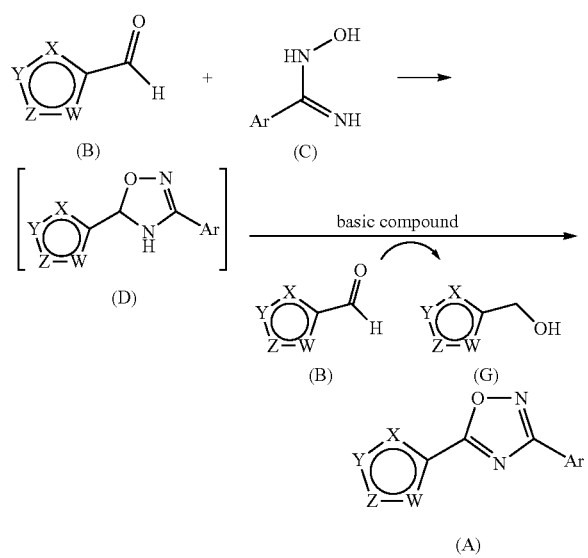

For efficient production of oxadiazole derivative A, it is preferable that compound B exists in the reaction system after the reaction of compound B and compound C. Therefore, in the reaction of compound B and compound C, compound B is preferably used in a larger amount than the theoretical amount. Specifically, compound B is reacted preferably in an amount exceeding 1 mol, preferably 1.5 mol or more, more preferably 1.8 mol or more, further more preferably 2.0 mol or more, particularly preferably 2.05 mol or more, per 1 mol of compound C. In addition, it is preferably 10 mol or less, more preferably 5 mol or less, further more preferably 3 mol or less, from the aspect of economic efficiency.

Such oxidation-reduction reaction of compound D and compound B is considered to proceed, for example, by Cannizzaro reaction type reaction mechanism.

In the present invention, compound B acts as an oxidant in the oxidation reaction from compound D to oxadiazole derivative A. Where necessary, the other oxidant may be used with compound B. As the other oxidant, the below-mentioned oxidant for the reaction of compound B and compound C can be used.

As the method of the separation of compound G from the reaction product, separation methods generally used can be employed. Examples of the separation method include liquid separation, filtration, distillation, recrystallization, reprecipitation, chromatography treatment and the like. When oxadiazole derivative A is solid, and compound G is liquid, the separation is preferably performed by filtration and washing, from the aspect of handling.

Compound G can be collected as compound B by subjecting compound G separated from the reaction product to an oxidation reaction, and the compound can be reused for the above-mentioned reaction of compound B and compound C. In this case, additional compound B may be used, if necessary. Therefore, in the present invention, compound G can be effectively used, and thereby, the efficiency in production method can be improved.

The oxidation reaction of compound G can be performed according to the known method described in literature (e.g., Organic Process Research & Development, 16(5), 1082-1089, 2012). The oxidation reaction of compound G can be performed by contacting compound G with an oxidant. Examples of the oxidant include hypochlorites such as sodium hypochlorite, potassium hypochlorite and the like, Oxone, hydrogen peroxide, oxygen and the like. The oxidation reaction of compound G may be performed in the presence of a catalyst such as iron oxide, iron sulfate, rhodium catalyst and the like. The oxidation reaction of compound G may be performed in the presence of a solvent. The amount of the oxidant can be appropriately changed depending on the kinds of the oxidant, and it is preferably 1 mol or more, more preferably 1.1 mol or more, further more preferably 1.2 mol or more, per 1 mol of compound G. The upper limit of the amount of the oxidant is preferably 10 mol, more preferably 5 mol, further more preferably 2 mol, per 1 mol of compound G. Examples of the solvent include water, ethyl acetate, chloroform and the like. The amount of the solvent is preferably 1 to 10-fold amount, preferably particularly 3 to 8-fold amount, relative to the volume of compound G. The temperature of the oxidation reaction is preferably 0° C. or above, more preferably 10° C. or above, and is preferably 30° C. or below, more preferably 20° C. or below. The reaction time varies depending on the reaction temperature and the reaction pressure, and it is preferably 1 to 5 hr. The reaction pressure may be normal pressure, increased pressure or reduced pressure, preferably normal pressure or increased pressure. The reaction pressure is preferably 0.01 to 0.5 MPa (gauge pressure). The reaction atmosphere may be an air atmosphere, or an inert gas atmosphere nitrogen and the like.

The reaction of compound B and compound C may be performed in the presence of an oxidant. The oxidant contributes to an oxidation reaction of compound D produced in the reaction of compound B and compound C.

Examples of the oxidant include hydrogen peroxide, manganese dioxide, 2,3-dichloro-5,6-dicyano-p-benzoquinone (DDQ), hypochlorous acid, potassium peroxodisulfate, oxygen, chlorine and the like.

While the timing of the addition of the oxidant is not limited, compound B and compound C may be reacted in the reaction system in which the oxidant exists in advance, or the oxidant may be added to the reaction system in which compound B and compound C exist. The amount of the oxidant can be appropriately changed depending on the kinds of the oxidant and the like, and it is preferably 1 mol or more, particularly preferably 1.5 mol or more, per 1 mol of compound C. The upper limit of the amount of the oxidant is preferably 10 mol, more preferably 5 mol, particularly preferably 2 mol, per 1 mol of compound C.

When the oxidant is used, the amount of compound B is preferably an amount exceeding 1 mol, more preferably 1.05 mol or more, particularly preferably 1.1 mol or more, per 1 mol of compound C, and is preferably 3 mol or less, particularly preferably 2.5 mol or less, per 1 mol of compound C.

In the present invention, compound B also shows an oxidation action as mentioned above, and therefore, use of an oxidant is not essential.

Preferable embodiments of the production method of the present invention are the following embodiments.

(1) the production method of oxadiazole derivative A by reacting compound B and compound C in the presence of a basic compound, (2) the production method of oxadiazole derivative A and compound G by reacting compound B and compound C in the presence of a basic compound to obtain a reaction product containing oxadiazole derivative A and compound G, and by isolating each of oxadiazole derivative A and compound G from the reaction product, (3) the production method of oxadiazole derivative A by subjecting compound G in the method of (2) to oxidation to obtain compound B, and by reacting the obtained compound B with compound C in the presence of a basic compound, and (4) the production method of oxadiazole derivative A wherein compound C in the above-mentioned (1) to (3) is produced by reacting compound F and hydroxylamine.

The concept of the preferable embodiment is shown in the following formula.

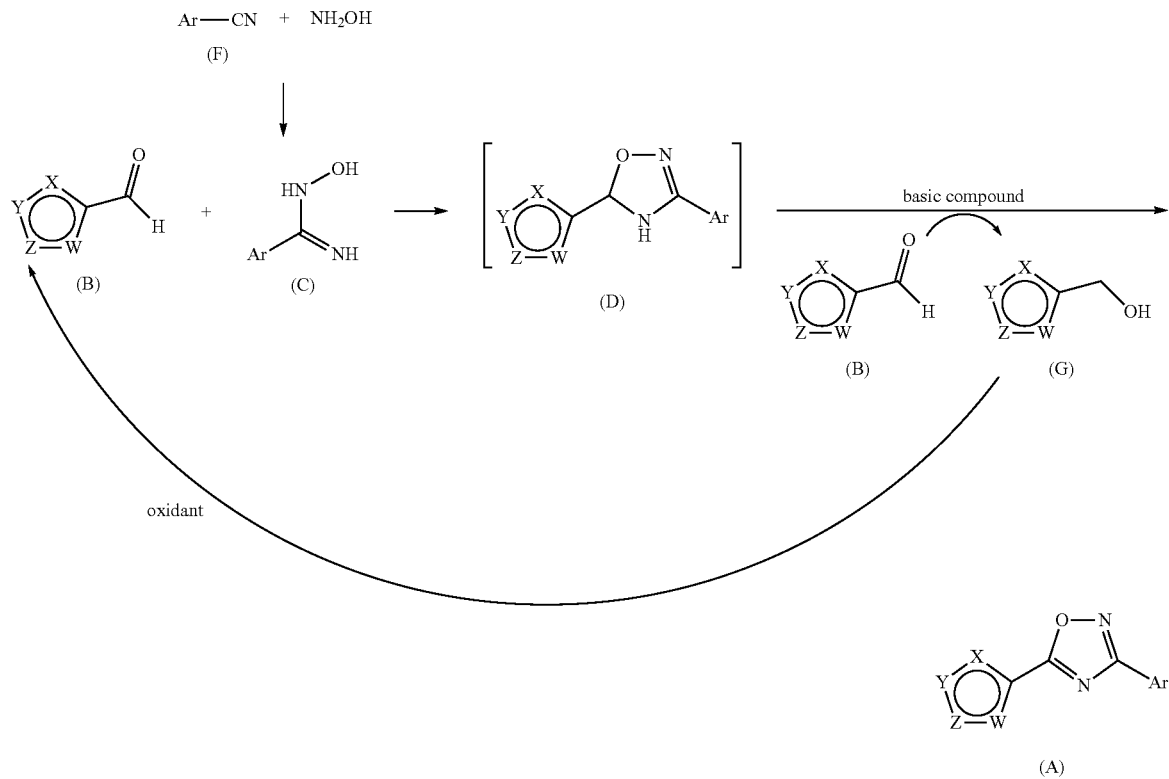

In the production method of the present invention, pre-treatments such as dehydration treatment, purification treatment and the like may be performed before use of each compound or before next step, and post-treatments such as isolation treatment, purification treatment and the like may be performed after reaction.

Oxadiazole derivative A obtained by the production method of the present invention is preferably subjected to purification treatment to obtain oxadiazole derivative A with purity depending on the purpose. As the purification treatment method, publicly or commonly known purification method such as liquid separation, filtration, distillation, recrystallization, reprecipitation, chromatography treatment and the like can be employed.

According to the production method of the present invention, the oxadiazole derivative A can be produced in yield of 50 mol % or more, preferably 70 mol % or more, more preferably 80 mol % or more, on the basis of (C).

The oxadiazole derivative A obtained by the production method of the present invention has a high physiological activity, and is a compound useful in medical or agrochemical field.

EXAMPLES

The present invention is explained in detail in the following by referring to Examples, which are not to be construed as limitative. In Example, % means mol %

[Quantitative Analysis]

In each Example, analysis using high-performance liquid chromatography (HPLC) was performed under the following condition.

Analysis using HPLC was performed under the following condition.

apparatus: Agilent Technologies 1260 Infinity column: YMC-Pack ODS-AM AM12S05-1546WT (150× 4.6 mmI.D., S-5 μm, 12 nm)

flow rate: 0.6 ml/min eluent: 0.1% phosphate buffer solution (0.1% $Et_3$+$H_3PO_4$ aq):$CH_3CN$=50:50 to 20:80 (0-20 min), 20:80 (20-30 min)

detector: diode array detector, measurement wavelength: 254 nm

Example 1

Thiophene-2-carboaldehyde (2-formylthiophene: 1.02 g, 9.1 mmol) and ethanol (14 mL; boiling point 78° C.) were charged into a glass egg-plant shaped flask to give a mixture. To the mixture were added benzamidoxime (1.25 g, 9.2 mmol) and potassium carbonate (0.13 g, 0.94 mmol), and the mixture was heated under reflux with stirring for 30.5 hr. The precipitated solid was collected by filtration, and washed with ethanol and water to give 3-phenyl-5-(thiophen-2-yl)-1,2,4-oxadiazole represented by the following formula (hereinafter to be referred to as compound A-1) in yield of 33% (on the basis of the amount of thiophene-2-carboaldehyde).

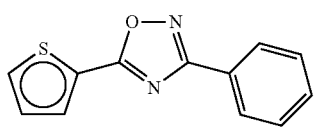

(A-1)

Example 2

Thiophene-2-carboaldehyde (2.02 g, 18.0 mmol) and ethanol (9 mL) were charged into a glass egg-plant shaped flask to give a mixture. To the mixture were added benzamidoxime (1.23 g, 9.0 mmol) and potassium hydroxide (0.053 g, 0.95 mmol), and the mixture was heated under reflux with stirring for 30 hr. It was confirmed that compound A-1 was obtained in yield of 73% (on the basis of the amount of benzamidoxime) by quantitative analysis using HPLC.

Example 3

Thiophene-2-carboaldehyde (2.12 g, 18.9 mmol) and dimethyl sulfoxide (9 mL) were charged into a glass egg-plant shaped flask to give a mixture. To the mixture were added benzamidoxime (1.23 g, 9.03 mmol) and potassium hydroxide (0.058 g, 1.03 mmol), and the mixture was heated with stirring at 78° C. for 30 hr. It was confirmed that compound A-1 was obtained in yield of 66% (on the basis of the amount of benzamidoxime) by quantitative analysis using HPLC.

Example 4

Thiophene-2-carboaldehyde (2.12 g, 18.9 mmol) and sulfolane (9 mL) were charged into a glass egg-plant shaped flask to give a mixture. To the mixture were added benzamidoxime (1.23 g, 9.00 mmol) and potassium hydroxide (0.12 g, 2.13 mmol), and the mixture was heated with stirring at 78° C. for 15 hr. It was confirmed that compound A-1 was obtained in yield of 90% (on the basis of the amount of benzamidoxime) by quantitative analysis using HPLC.

Example 5

Thiophene-2-carboaldehyde (42.7 g, 380 mmol) and t-amyl alcohol (39.9 g) were charged into a glass egg-plant shaped flask to give a mixture. To the mixture were added benzamidoxime (24.5 g, 180 mmol) and potassium hydroxide (2.42 g, 43.1 mmol), and the mixture was heated under reflux for 1.5 hr, with dehydration treatment using molecular sieve. It was confirmed that compound A-1 was obtained in yield of 95% (on the basis of the amount of benzamidoxime) by quantitative analysis using HPLC.

Example 6

Thiophene-2-carboaldehyde (42.0 g, 375 mmol) and t-amyl alcohol (39.9 g; boiling point 102° C.) were charged into a glass egg-plant shaped flask to give a mixture. To the mixture were added benzamidoxime (24.4 g, 179 mmol) and potassium carbonate (4.98 g, 36.0 mmol), and the mixture was heated under reflux for 3 hr, with dehydration treatment using molecular sieve. It was confirmed that compound A-1 was obtained in yield of 96% (on the basis of the amount of benzamidoxime) by quantitative analysis using HPLC.

Example 7

Thiophene-2-carboaldehyde (21.1 g, 188 mmol) and t-amyl alcohol (19.9 g) were charged into a glass egg-plant shaped flask to give a mixture. To the mixture were added benzamidoxime (12.2 g, 89.6 mmol) and potassium hydroxide (1.20 g, 21.4 mmol), and the mixture was heated under reflux with stirring for 30 hr. It was confirmed that compound A-1 was obtained in yield of 94% (on the basis of the amount of benzamidoxime) by quantitative analysis using HPLC.

Example 8

Thiophene-2-carboaldehyde (2.12 g, 18.9 mmol) and sulfolane (10.8 g) were charged into a glass egg-plant shaped flask to give a mixture. To the mixture were added benzamidoxime (1.22 g, 8.96 mmol) and potassium hydroxide (0.593 g, 10.6 mmol), and the mixture was heated with stirring at 78° C. for 4 hr. It was confirmed that compound A-1 was obtained in yield of 55% (on the basis of the amount of benzamidoxime) by quantitative analysis using HPLC.

Example 9

Benzamidooxime (297 g, 2.18 mol), potassium hydroxide (11.7 g, 0.208 mol) and t-amyl alcohol (1.22 kg) were charged into a glass egg-plant shaped flask to give a mixture. The mixture was subjected to azeotropic dehydration treatment by heating under reflux with stirring. To the obtained mixture was added thiophene-2-carboaldehyde (446 g, 3.97 mol), and the mixture was heated under reflux for 3 hr, with azeotropic dehydration. It was confirmed that compound A-1 was obtained in yield of 100% (on the basis of the half amount of thiophene-2-carboaldehyde; the yield on the basis of the amount of benzamidoxime was 91%) by quantitative analysis using HPLC.

Example 10

Thiophene-2-carboaldehyde (2.12 g, 18.9 mmol) and sulfolane (10.8 g; 8.6 ml) were charged into a glass egg-plant shaped flask to give a mixture. To the mixture were added benzamidoxime (1.22 g, 8.99 mmol) and potassium hydroxide (0.296 g, 5.27 mmol), and the mixture was heated with stirring at 78° C. for 4 hr. It was confirmed that compound A-1 was obtained in yield of 84% (on the basis of the amount of benzamidoxime) by quantitative analysis using HPLC.

Example 11

The solution containing compound A-1 and thiophene-2-methanol, which was obtained in Example 9, was filtered to give compound A-1 in yield of 97% (on the basis of the half of amount of thiophene-2-carboaldehyde used in Example 9). In addition, the thiophene-2-methanol was collected in yield of 46% on the basis of the amount of thiophene-2-carboaldehyde used for the reaction. The collected thiophene-2-methanol was subjected to an oxidation reaction with sodium hypochlorite to give thiophene-2-carboaldehyde in yield of 87%.

Example 12

Benzonitrile (451 g, 4.38 mol), t-amyl alcohol (951 g) and water (241 g) were charged into a glass egg-plant shaped flask to give a mixture. To the mixture was added 50% aqueous hydroxylamine solution (360 g, 5.45 mol), and the mixture was heated with stirring at 50° C. for 3 hr to give a solution containing benzamidoxime. It was confirmed that benzamidoxime represented by the following formula (C-1) was obtained in yield of 100% by quantitative analysis using HPLC.

Example 13

The reaction was performed in the same manner as in Example 12, except that thiophene-2-carboaldehyde obtained in Example 11 was used instead of the commercially available product used in Example 12. It was confirmed that compound A-1 was obtained in yield of 100% (on the basis of the half amount of thiophene-2-carboaldehyde) by analysis of the product using HPLC.

Examples 14 to 16

The reaction was performed in the same manner as in Example 10, except that piperidine was used as a basic compound, the kind of the solvent, the charging ratio and the reaction time were changed. The results were collectively shown in Table 1.

TABLE 1

| Ex. | Compound (b)/ Compound (c) [mol/mol] | Basic Compound kind | Basic Compound/ Compound (c) [mol/mol] | Solvent kind | Temperature ° C. | Dehydration Treatment | Reaction Time [hr] | Yield [%] |
|---|---|---|---|---|---|---|---|---|
| 1 | 0.99 | potassium carbonate | 0.10 | ethanol | reflux temperature | non | 30 | 33% |
| 2 | 2.09 | potassium hydroxide | 0.11 | ethanol | reflux temperature | non | 30 | 73% |
| 3 | 2.10 | potassium hydroxide | 0.11 | dimethyl sulfoxide | 78 | non | 30 | 66% |
| 4 | 2.10 | potassium hydroxide | 0.24 | sulfolane | 78 | non | 15 | 90% |
| 5 | 2.11 | potassium hydroxide | 0.24 | t-amyl alcohol | reflux temperature | preformed | 1.5 | 95% |
| 6 | 2.09 | potassium carbonate | 0.20 | t-amyl alcohol | reflux temperature | preformed | 3 | 96% |
| 7 | 2.10 | potassium hydroxide | 0.24 | t-amyl alcohol | reflux temperature | non | 30 | 94% |
| 8 | 2.11 | potassium hydroxide | 1.18 | sulfolane | 78 | non | 4 | 55% |
| 9 | 1.82 | potassium hydroxide | 0.10 | t-amyl alcohol | reflux temperature | preformed | 3 | 91% |
| 10 | 2.11 | potassium hydroxide | 0.59 | sulfolane | 78 | non | 4 | 84% |
| 14 | 1.50 | piperidine | 0.08 | toluene | reflux temperature | non | 30 | 20% |
| 15 | 1.50 | piperidine | 0.08 | t-amyl alcohol | reflux temperature | non | 30 | 24% |
| 16 | 2.10 | piperidine | 1.00 | t-amyl alcohol | reflux temperature | non | 30 | 76% |

* In the table, compound (b) is thiophene-2-carboaldehyde, and compound (c) is benzamidoxime.
* The yield is calculated on the basis of compound (c).

The reaction was performed in the same manner as in Example 9, except that the obtained benzamidoxime solution was used instead of the benzamidoxime used in Example 9. It was confirmed that compound A-1 was obtained in yield of 100% (on the basis of the half amount of thiophene-2-carboaldehyde) by analysis of the product using HPLC.

(C-1)

INDUSTRIAL APPLICABILITY

According to the present invention, the production method of 1,2,4-oxadiazole derivatives, which is performed by easy procedures and with high production efficiency, can be provided.

This application is based on patent application No. 2015-044489 filed on Mar. 6, 2015 and No. 2015-223822 filed on Nov. 16, 2015 in Japan, the contents of which are encompassed in full herein.

The invention claimed is:

1. A method of producing a 1,2,4-oxadiazole derivative represented by the following formula (A), which comprises reacting a compound represented by the following formula (B) and a compound represented by the following formula (C) in the presence of a basic compound;

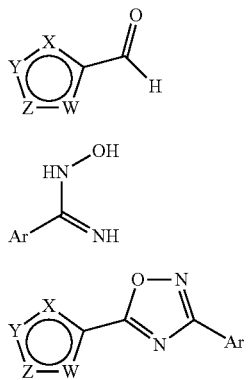

wherein
Ar is an aromatic group or an aromatic group having substituent(s),
W, X, Y and Z are each independently —S—, —N=, —CH= or —CR=, and one selected from W, X, Y and Z is —S—, and
R is an alkyl group having 1 to 5 carbon atoms, an alkoxy group having 1 to 3 carbon atoms, a haloalkyl group having 1 to 3 carbon atoms, a haloalkoxy group having 1 to 3 carbon atoms or a halogen atom.

2. The method according to claim 1, wherein the compound represented by the formula (B) is a compound represented by the following formula (B¹), and the 1,2,4-oxadiazole derivative represented by the formula (A) is a compound represented by the following formula (A¹);

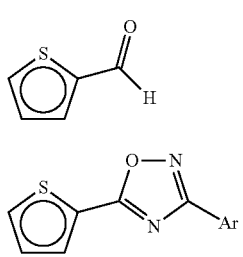

wherein Ar is as defined in claim 1.

3. The method according to claim 1, wherein Ar is a phenyl group or a phenyl group having substituent(s).

4. The method according to claim 1, wherein the reaction of the compound represented by the formula (B) and the compound represented by the formula (C) is performed in the presence of a solvent.

5. The method according to claim 1, wherein the reaction of the compound represented by the formula (B) and the compound represented by the formula (C) is performed with dehydration.

6. The method according to claim 1, wherein the compound represented by the formula (B) is reacted in an amount exceeding 1 mol, per 1 mol of the compound represented by the formula (C).

7. The method according to claim 1, wherein the basic compound is at least one inorganic basic compound selected from the group consisting of an alkali metal carbonate, an alkaline-earth metal carbonate, an alkali metal hydroxide and an alkaline-earth metal hydroxide.

8. The method according to claim 7, wherein the inorganic basic compound is used in an amount of 2 mol or less, per 1 mol of the compound represented by the formula (C).

9. The method according to claim 1, wherein the basic compound is an organic basic compound, and the organic basic compound is used in an amount of 0.3 mol or more, per 1 mol of the compound represented by the formula (C).

10. The method according to claim 1, wherein the compound represented by the formula (C) is obtained by reacting a compound represented by the following formula (F) with hydroxylamine, and then the obtained compound is reacted with the compound represented by the formula (B);

Ar—CN         (F)

wherein Ar is as defined in claim 1.

11. The method according to claim 1, wherein the compound represented by the formula (C) is subjected to dehydration, and then reacted with the compound represented by the formula (B).

12. The method according to claim 10, wherein the compound represented by the formula (F) is reacted with hydroxylamine in a solvent to obtain a mixture of the compound represented by the formula (C) and the solvent, and then the obtained mixture is reacted with the compound represented by the formula (B).

* * * * *